United States Patent
Vertesy et al.

(10) Patent No.: US 6,627,604 B2
(45) Date of Patent: Sep. 30, 2003

(54) MEMNO PEPTIDES, PROCESS FOR THEIR PREPARATION AND USE THEREOF

(75) Inventors: Laszlo Vertesy, Eppstein-Vockenhausen (DE); Herbert Kogler, Glashütten (DE); Astrid Markus, Liederbach (DE); Matthias Schiell, Brechen (DE)

(73) Assignee: Aventis Pharma Deutschland, GmbH, Frankfurt am Main (DE)

( * ) Notice: Subject to any disclaimer, the term of this patent is extended or adjusted under 35 U.S.C. 154(b) by 108 days.

(21) Appl. No.: 09/794,346

(22) Filed: Feb. 28, 2001

(65) Prior Publication Data

US 2001/0031857 A1 Oct. 18, 2001

(30) Foreign Application Priority Data

Feb. 29, 2000 (EP) .............................. 00104114

(51) Int. Cl.$^7$ ............................ A61K 38/08; A61P 9/04; C07K 7/06; C12P 21/02
(52) U.S. Cl. ............................ 514/8; 435/71.1; 435/72; 435/119; 514/14; 514/15; 514/16; 514/17; 514/18; 514/19; 514/411; 514/416; 514/417; 530/322; 530/327; 530/328; 530/329; 530/330; 530/331; 548/430; 548/431
(58) Field of Search ..................... 435/71.1, 72, 119; 514/2, 8, 14, 15, 16, 17, 18, 19, 20, 25, 35, 411, 416, 417; 530/322, 327, 328, 329, 330, 331; 548/430, 431

(56) References Cited

U.S. PATENT DOCUMENTS 5,817,683 A * 10/1998 Elliott et al. ................. 514/381
6,197,780 B1 * 3/2001 Munter et al. ............... 514/274
6,197,800 B1 * 3/2001 Dorsch et al. ............... 514/362

FOREIGN PATENT DOCUMENTS

JP 08-283118 A * 10/1996
WO WO-99/05132 A1 * 2/1999
WO WO-99/29308 A2 * 6/1999

OTHER PUBLICATIONS

Ogawa et al. Stachybocins, Novel Endothelin Receptor Antagonists, Produced by Stachybotrys sp. M6222. The Journal Of Antibiotics. Dec. 1995, vol. 48, No. 12, pp. 1396–1400.*

Sakai et al. Isolation, Characterization and Biological Activities of Novel Triprenyl Phenols . . . The Journal Of Antibiotics. Jun. 1995, vol. 48, No. 6, pp. 447–456.*

Roggo, B.E., et al., "Novel Spirodihydrobenzofuranlactams as Antagonists of Endothelin and as Inhibitors of HIV–1 Protease Produced by Stachybotrys sp. I. Fermentation, Isolation and Biological Activity," The Journal of Antibiotics, 49(1):13–19 (1996).

Roggo, B.E., et al., "Novel Spirodihydrobenzofuranlactams as Antagonists of Endothelin and as Inhibitors of HIV–1 Protease Produced by Stachybotrys sp. II Structure Determination," The Journal of Antibiotics, 49(4):374–379 (1996).

Algenstaedt, P., et al. "Insulin Receptor Substrate Proteins Create a Link between the Tyrosine Phosphorylation Cascade and the $CA_{2+}$–ATPases in Muscle and Heart," The Journal of Biological Chemistry, 272(38):23696–23702 (1997).

Simmerman, H.K.B., et al., "Phospholamban: Protein Structure, Mechanism of Action, and Role in Cardiac Function," Physiological Reviews, 78(4):921–947 (1998).

Ogawa, K., et al., "Stachybocins, Novel Endothelin Receptor Antagonists, Produced by Stachybotrys sp. M6222 II. Structure Determination of Stachybocins A,B, and C," The Journal of Antibiotics, 48:1396–1400 (1995).

Nozawa, Y., et al., "Stachybotrin C and Parvisporin, Novel Neuritogenic Compounds I. Taxonomy, Isolation, Physicochemical and Biological and Biologica Prperties," The Journal of Antibiotics, 50:(8):635–645 (1997).

Kobayashi, J., et al., "Nakijiquinones C and D, New Sesquiterpenoid Quinones with a Hydroxy Amino Acid Residue from a Marine Sponge Inhibiting c–erbB–2 Kinase," Tetrahedron, 51(40):10867–10874 (1995).

* cited by examiner

Primary Examiner—Jeffrey E. Russel
(74) Attorney, Agent, or Firm—Finnegan, Henderson, Farabow, Garrett & Dunner, LLP

(57) ABSTRACT

The invention relates to novel peptide derivatives, called memno peptides, of the formula (I):

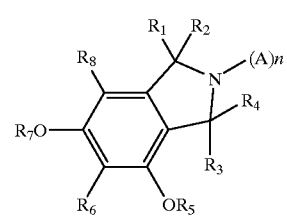

wherein $R_1$, $R_2$, $R_3$, $R_4$, $R_5$, $R_6$, $R_7$, $R_8$ and (A)n have the meaning herein, obtainable by cultivation of Memnoniella echinata FH2272, DSM 13195 or mutants and variants of this, a process for their preparation and the use of the compounds as pharmaceuticals, for example against cardiac insufficiency.

34 Claims, No Drawings

MEMNO PEPTIDES, PROCESS FOR THEIR PREPARATION AND USE THEREOF

The invention relates to novel peptide derivatives, called memno peptides, obtainable by fermentation of *Memnoniella echinata* FH2272, DSM 13195, in a culture medium, a process for the preparation of the memno peptides, and the use of the memno peptides as pharmaceuticals, for example, for the production of a pharmaceutical for the treatment of cardiac insufficiency.

Cardiovascular disorders still rank first as causes of death in the western industrial countries. A not inconsiderable proportion of these are patients with the diagnosis of cardiac insufficiency. Cardiac insufficiency is understood as meaning the inadequate functioning of the heart. The heart is not able to produce an output corresponding to the mammal's requirements. Cardiac insufficiency is an acute or chronic inability of the heart, under load or even at rest, to muster the blood output necessary for metabolism or to take up the venous return. It is the state of the heart wherein the compensation mechanisms, such as heart rate, stroke volume, or hypertension, no longer suffice for the maintenance of a normal cardiac output. Cardiac insufficiency has a variety of causes, for example inflammatory and degenerative myocardial (heart muscle) changes, coronary circulatory disorders and cardiac infarct. Cardiac insufficiency leads to changes in the peripheral circulation, to impairment of the respiration, the kidney function, and the electrolyte balance, and also to reduced power of the skeletal musculature, and in the end it frequently leads to death.

Cardiac insufficiency generally occurs at an advanced age. The incidence is 3 disorders per 1000 inhabitants per year in 35–64 year-olds and 10/1000/year in the age group from 65 to 94 years. Mortality increases in 75-year-olds almost by a factor of 200 compared with the age group between 35 and 44 years. The mortality rate has remained approximately constant between 1970 and 1983, as investigations in the USA showed. For the Federal Republic of Germany, the same numbers are to be assumed. More than 50% of patients die in the first five years after diagnosis. This statistical examination, in and of itself, shows the great importance of cardiac insufficiency for the population, but it also confirms the inadequate possibilities of medicinal treatment which are available to the physician today.

In view of the inadequacy of present treatments, new concepts have been developed which should lead to innovative cardiac remedies. The ability of the cardiac and skeletal muscles to contract and thus to perform mechanical work is dependent on (1) contractile structural elements (myofibrils) and (2) chemical energy (ATP) available to the myofibrils, which is converted into mechanical energy in the contraction process. Shortening of the myofibrils occurs in the contraction process. This may be initiated by motor nerve impulses, under the action of which calcium ions ($Ca^{2+}$) enter into the sarcoplasmatic space from the extracellular space within a few milliseconds and the calcium depots are emptied. In myocardial insufficiency (cardiac insufficiency), the $Ca^{2+}$ concentration in myofibrils may be reduced. $Ca^{2+}$ ions, however, are indispensable for the activation of the contractile apparatus. If there is increased demand, $Ca^{2+}$ is generally pumped into the sarcoplasmatic reticulum (SR) under catalysis of a membranous $Ca^{2+}$-dependent $Mg^{2+}$-ATPase: this enzyme is also called Sarco(Endo)plasmatic Reticulum $Ca^{2+}$ATPase (SERCA2). According to hydropathic analysis, the $Ca^{2+}$ATPase comprises ten transmembranous helices and a number of extramembranous loops. On the cytosolic side, domains for $Ca^{2+}$ and ATP binding, for phosphorylation and for interaction with the modulator protein phospholamban (PLB) are formed. The latter is a protein pentamer, which is localized in the membrane of the SR and exerts an inhibitory influence on SERCA2 in the unphosphorylated state. Under physiological stress, a phosphorylation of PLB takes place, which increases the $Ca^{2+}$ affinity of SERCA2a and thus increases the transport rate for $Ca^{2+}$ ions in the SR. The phosphorylation of PLB (a 52 amino acid protein) takes place on two amino acid residues: serine-16 may be phosphorylated by the cAMP-dependent protein kinase and threonine may be phosphorylated in position 17 by the $Ca^{2+}$/calmodulin-dependent kinase. This phosphorylation causes a change in confirmation in PLB followed by an increased affinity of SERCA2 for $Ca^{2+}$. Anti-PLB antibodies are able to imitate the PLB phosphorylation effect and thus confirm the key role of PLB as a regulator of the contractile activity of the heart (Phospholamban: Protein Structure, Mechanism of Action and Role in Cardiac Function. H. K. Simmerman and L. R. Jones, Physiological Reviews; Vol. 78, No. 4, 921ff, 1998). Activators of SERCA2 should thus bring about a favorable influence in cardiac insufficiency.

It has surprisingly been found that cultures of the fungal strain *Memnoniellla echinata* FH 2272, DSM 13195 contain natural substances which are able to display favorable effects on the heart and the circulation. The isolated active compounds, the memno peptides, are natural substances comprising specific constituent groups. These consituent groups include terpene units, a so-called polyketide moiety and a nitrogen-containing group.

Terpenes are naturally occurring compounds which can be interpreted formally as polymerization products of the hydrocarbon isoprene. According to the number of isoprene groups, monoterpenes ($C_{10}$), sesquiterpenes ($C_{15}$), diterpenes ($C_{20}$) etc. can be differentiated. A large number of compounds can be formed from the parent structures by substitution, cyclization, rearrangement, oxidation etc.; accordingly, many thousands of terpenes have been described in the literature. Nitrogen-containing compounds originating from the terpenes have also been reported, but these are counted among the alkaloids (e.g. the Gentiana alkaloids) [Römpp Chemie Lexikon [Römpp's Chemical Encyclopedia], 9th Edition, Volume 6, page 4508 ff., Georg Thieme Verlag, Stuttgart/New York, 1992]. These terpenes, however, differ fundamentally from the memno peptides according to the invention, wherein terpenes do not contain a polyketide moiety with which they can bind nitrogen.

Examples of further, known nitrogen-containing terpenes are:

Stachybocins [J. Antibiotics, 48: 1396 (1995)];
Stachybotrins [Y. Nozawa et al. J. Antibiotics, 50: 635–645 (1997)];
*Spirodihydrobenzofuran lactams*[J. Antibiotics, 49: 13 (1996)];
Nakijiquinones [Tetrahedron, 51: 10867–10874 (1995)];
F1839-A to J are nitrogen-containing terpenes having polyketide moieties [Japanese Patent 061864133 and 08283118]. They are cholesterol esterase inhibitors.

These terpene derivatives were synthesized from various strains of the genera *Memnoniella echinata* and Stachybotrys and others. They were described as antagonists of the endothelin receptor, as inhibitors of HIV-1 protease and of cholesterol esterase and as hair tonics. The inositol monophosphatase inhibitor L-671,776 was moreover isolated from cultures of the strain *Memnoniella echinata*, ATCC 20928 [Y. K. T. Lam et al. J. Antibiotics, 45, pp.1397–1402, (1992)].

The memno peptides according to the invention have a differing spectrum of activity. A conspicuous feature is their activating effect on SERCA2 and thus on the insufficient heart.

The present invention thus relates to compounds of formula (I)

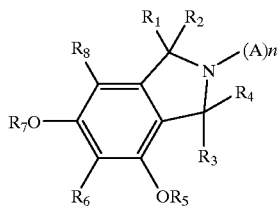

I wherein
$R_1$ and $R_2$ together are double bonded O, or $H_2$, or H and OH, or H and O—$C_1$—$C_4$-alkyl;
$R_3$ and $R_4$ together are double bonded O, or $H_2$, or H and OH, or H and O—$C_1$—$C_4$-alkyl;
$R_8$ is chosen from H, OH, $C_1$—$C_4$-alkyl and O—$C_1$—$C_4$-alkyl, such as O-methyl; $R_6$ is a group of formula (II)

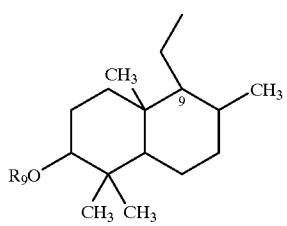

II wherein $R_9$ is H or a glycosidically bonded sugar, or a group of the formula (III)

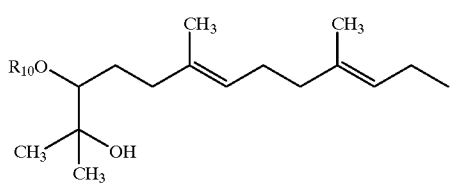

III wherein $R_{10}$ is H or a glycosidically bonded sugar, and wherein,
if $R_6$ is a group of the formula (II), then $R_5$ is a bond to the carbon atom C9 of the formula (II) and $R_7$ is H, or $R_7$ is a bond to the carbon atom C9 of the formula (II) and $R_5$ is H, and
if $R_6$ is a group of the formula III, then $R_5$ and $R_7$ are H;
A is an amino acid,
n is an integer chosen from 1 to 12, wherein each A is the same or different from every other A, wherein the nitrogen atom in the isoindole ring of formula (I) is the N-terminal amine nitrogen of the first amino acid of the (A)n group;

or a salt or derivative thereof;

with the proviso that

A is an amino acid other than Glu when n is 1, and $R_1$ and $R_2$ together are double bonded O, and $R_3$ and $R_4$ together are $H_2$, and $R_6$ is a group of formula (II), and $R_5$ is a bond to the carbon atom C9 of the group of formula (II), and $R_7$ is H, and $R_8$ is H and $R_9$ is H.

In formula (I), (A)n can be at least one natural amino acid selected from: Gly, Ala, Val, Leu, Ile, Pro, Ser, Thr, Phe, Tyr, Trp, Lys, Arg, Asp, His, Glu, Asn, Gln, Cys and Met. (A)n can be a peptide chain having from 2 to 12 amino acids. In one embodiment (A)n comprises 10 amino acids.

$C_1$–$C_4$-Alkyl is a straight-chain or branched alkyl having 1 to 4 carbon atoms, such as methyl, ethyl, i-propyl and tert-butyl.

The sugar can be a hexose, for example an aldohexose, such as mannose, glucose or galactose, which may be optionally substituted with additional groups, such as $C_1$ to $C_4$-Alkyl or $NH_2$.

The present invention furthermore relates to all obvious derivatives of the compounds of the formula I. Derivatives are salts, reduction products, esters, ethers, acetals as well as amides and N-alkylation products, moreover all optical antipodes, diastereomers and all stereomeric forms.

In one embodiment, the compound of formula (I) has formula (IV)

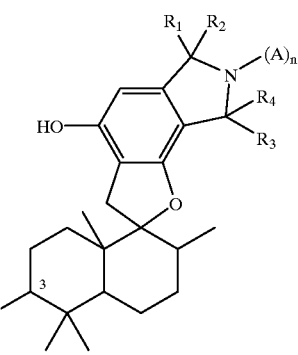

IV where the groups $R_1$, $R_2$, $R_3$, $R_4$, $R_9$ and (A)n have the meaning as indicated above.

In the formula (IV), $R_1$ and $R_2$ taken together can be double bonded O, $R_3$ and $R_4$ together can be $H_2$ and $R_9$ can be H.

In one embodiment, the inventive compound is memno peptide A, $C_{76}H_{108}N_{16}O_{18}S$, of the formula (IVa)

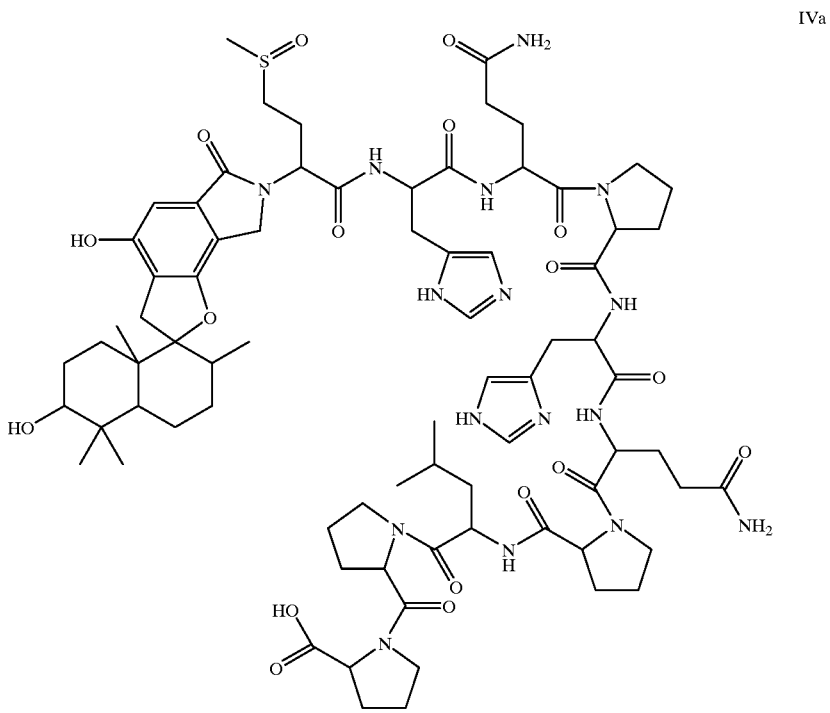

In this formula, the decalin structure having the 4-methyl and a methylene group is the terpene moiety; the substituted isoindole ring is the ketide moiety. The amino acid sequence:
Met His Gln Pro His Gln Pro Leu Pro Pro (SEQ ID NO:1) is a part of the casein sequence. The methionine (Met) can be oxidized to the sulfoxide.

Formula (IVb) shows a preferred spatial form:

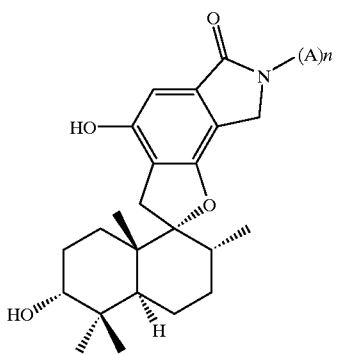

wherein (A)n has the meaning as indicated above.

The physicochemical and spectroscopic properties of the preferred compound according to the invention can be summarized as follows:

Memno peptide A

Appearance: colorless substance soluble in polar organic solvents and in water. It is stable in neutral, mildly acidic medium.

Empirical formula: $C_{76}H_{108}N_{16}O_{18}S$,

Molecular weight: 1565.87 Da,

UV absorption ($\lambda_{max}$): 270 nm,

NMR data: see Table 1

The numbering of the carbon atoms and the associated NMR chemical shifts are classified according to the numbering procedure for cyclic sesquiterpenes.

FIG. 1: Numbering of a cyclic sesquiterpene ketolide.

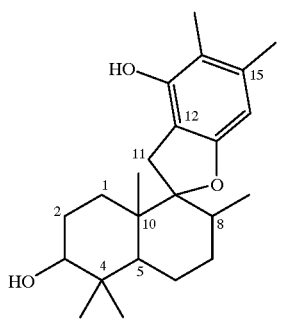

TABLE 1

NMR data (chemical shifts) of memno peptide A in DMSO - $d_6$ at 310K.

| | δ-$^{13}$C | m | δ-$^1$H | m | $^n$J$_{HH}$ | $^n$J$_{CH}$ (10 Hz) | assignment |
|---|---|---|---|---|---|---|---|
| 1 | 15.42 | q | 0.668 | d | 1.802 | 1.802 | Terpene-8-Me |
| 2 | 15.72 | q | 0.978 | s | — | 2.035, 1.763 | Terpene-10-Me |
| 3 | 20.37 | t | 1.409 | m | 2.035, 1.538 | 2.035 | Terpene-6 |
| | | | 1.460 | | 2.035, | | |
| 4 | 21.43 | q | 0.873 | d | 1.678 | 1.678, 1.428, 0.890 | Leu$^8$-δ |
| 5 | 22.25 | q | 0.827 | s | 0.918 | 0.918, 2.035 | Terpene-4-Me |
| 6 | 22.64 | t | 2.182 | ddt | 4.892, 2.788 2.632 | 4.892, 2.788, 2.632 | Met$^1$-β |
| | | | 2.307 | ddt | | | |
| | 22.80 | t | 2.19 | ddt | 4.869, 2.757, 2.635 | 4.869, 2.757, 2.635 | |
| | | | 2.31 | ddt | | | |
| 7 | 23.08 | q | 0.890 | d | 1.678 | 1.678, 1.428, 0.873 | Leu$^8$-δ' |
| 8 | 23.88 br | d | 1.678 | m | 0.87, 0.88 | | Leu$^B$-γ |
| 9 | 23.90 | t | 1.764 | m | 0.962, 1.416, 1.871 | 0.978, 1.416, 3.227 | Terpene-1 |
| | | | 0.962 | m | | | |
| 10 | 24.22 | t | 1.910 | m | 2.144, 4.588, 3.467 | 2.144, 1.771, 4.588, 3.467, 3.689 | Pro$^9$-γ |
| 11 | 24.32 | t | 1.863 | m | 2.031, 1.798, 3.625 | 4.356, 3.625, 2.153, 1.792 | Pro$^4$-γ |
| 12 | 24.37 | t | 1.927 | m | (2.153), (1.814), 3.624 | 4.388, 3.624, 1.814 | Pro$^7$-γ |
| 13 | 24.43 | t | 1.926 | m | 2.144, 1.840, 3.655, 3.538 | 4.224, 3.655, 3.538 | Pro$^{10}$-γ |
| 14 | 24.77 | t | 1.840 | m | 1.416, 1.740, 0.962 | — | Terpene-2 |
| | | | 1.416 | m | 1.840, 0.926 | | |
| 15 | 26.51 | t | 1.940 | m | 1.719, 4.484, 2.198 | 2.198 | Gln$^3$-β |
| | | | 1.719 | m | 1.719, 4.484, 2.198 | | |
| 16 | 26.85 | t | 1.927 | m | 1.722, 4.468, 2.166 | 2.166 | Gln$^6$-β |
| | | | 1.722 | m | 1.927, 4.468, 2.166 | | |
| 17 | 27.04 br | t | 2.976 | dd | 4.598 | — | His$^5$-β |
| | | | 3.067 | dd | | | |
| 18 | 27.09 | t | 2.937 | dd | 4.570 | (4.570) | His$^2$-β |
| | | | 3.067 | dd | | | |
| 19 | 27.50 | t | 2.144 | m | 1.771, 4.578, 1.905, 1.945 | 1.945, 3.689, 3.467, 4.578 | Pro$^9$-β |
| | | | 1.771 | m | 2.144, 4.578, 1.905, 1.945 | | |
| 20 | 28.34 | t | 2.144 | m | 1.840, 4.223, 1.926 | 4.223, 3.669, 3.533 | Pro$^{10}$-β |
| | | | 1.840 | m | 2.144, 4.223, 1.926 | | |
| 21 | 28.50 | q | 0.918 | s | 0.827 | 0.827 | Terpene-4-Me |
| 22 | 28.86 | t | 1.798 | m | 4.356, 2.031, (1.863) | | Pro$^4$-β |
| | | | 2.031 | m | | | |
| 23 | 28.89 | t | 1.814 | m | 2.012, 4.388, (1.927) | 4.388, 3.646 | Pro$^7$-β |
| | | | | | 1.814, 4.388, (1.927) | | |
| | | | 2.012 | m | | | |
| 24 | 30.63 | t | 1.538 | m | 1.430, 1.460, (1.409), (1.802) | 0.667 | Terpene-7 |
| | | | 1.430 | m | 1.538, 1.460, 1.802 | | |
| 25 | 30.64 | t | 2.166 | t | 1.927, 1.722 | 1.927, 1.722, 4.466, 6.807 | Gln$^6$-γ |
| 26 | 30.65 | t | 2.192 | t | 1.940, 1.719 | 1.940, 1.719, 4.489, 6.789 | Gln$^3$-γ |
| 27 | 31.62 | t | 3.154 | d | 2.792 | 6.598 | Terpene-11 |
| | | | 2.792 | d | 3.154 | | |
| 28 | 36.43 | d | 1.802 | ddq | 1.538, 1.430, 0.667 | 0.667, 2.790, 3.156 | Terpene-8 |
| 29 | 37.22 | s | — | — | — | 0.903, 0.824 | Terpene-4 |
| 30 | 37.73 | q | 2.548 | s | — | 2.682, 2.758 | Met$^1$-ε |
| | 37.84 | | 2.546 | | | 2.633, 2.783 | |
| 31 | 39.45 | d | 2.035 | dd | 1.409, 1.460 | 0.903, 0.824, 0.971 | Terpene-5 |
| 32 | 40.07 | t | 1.428 | dt | 4.536, 1.678 | 0.890, 0.873, 4.536 | Leu$^8$-β |
| | 40.03 | | | | | | |
| 33 | 41.71 | s | — | — | — | 3.156, 2.790, 0.977, (1.764), 2.035 | Terpene-10 |
| 34 | 44.25 | t | 4.332 | — | — | 4.881 | Terpene-8' |
| 35 | 46.10 | t | 3.669 | | 1.934 | 4.223, 2.147, 1.934, 1.851 | Pro$^{10}$-δ |
| | | | 3.533 | | | | |
| 36 | 46.53 | t | 3.689 | m | 1.905, 1.936 | 4.588, 2.165, 1.781, 1.936 | Pro$^9$-δ |
| | | | 3.467 | m | | | |
| 37 | 46.81 | t | 3.624 | m | 1.927 | 1.814, 4.388 | Pro$^7$-δ |
| 38 | 46.87 | t | 3.644 | m | 1.863 | — | Pro$^4$-δ |
| 39 | 48.56 | d | 4.534 | dt | 7.918, 1.428 | 7.918, 1.428, 1.678 | Leu$^8$-α |
| 40 | 49.44 | t | 2.682, 2.758 | ddt ddt | 2.758, 2.162, 2.289 2.682, 2.162, 2.289 | 4.892, 2.550 | Met$^1$-γ |
| | 49.70 | t | 2.633, 2.783 | ddt ddt | 2.783, 2.289, 2.162 2.633, 2.289, 2.162 | 4.869, 2.545 | |
| 41 | 50.18 | d | 4.466 | dt | 8.110, 1.927, 1.722 | 2.166 | Gln$^6$-α |
| 42 | 50.31 | d | 4.484 | dt | 8.206, 1.935, 1.707 | 2.182 | Gln$^3$-α |
| 43 | 51.37 | d | 4.570 | ddd | 8.135, 2.975, 3.082 | 2.975, 3.082 | His$^5$-α |
| 44 | 51.68 | d | 4.590 | ddd | 8.496, 2.934, 3.067 | 2.934, 3.067 | His$^2$-α |

TABLE 1-continued

NMR data (chemical shifts) of memno peptide A in DMSO - $d_6$ at 310K.

| | δ-$^{13}$C | m | δ-$^{1}$H | m | $^nJ_{HH}$ | $^nJ_{CH}$ (10 Hz) | assignment |
|---|---|---|---|---|---|---|---|
| | | | 4.585 | | 8.506, 2.934, 3.067 | | |
| 45 | 53.30 | d | 4.892 | | 2.162, 2.284 | 2.162 | Met$^1$-α |
| | 53.62 | | 4.869 | | 2.162, 2.284 | | |
| 46 | 57.33 | d | 4.588 | dd | 2.144, 1.771 | 2.144, 1.771, 1.905, 1.945, 3.684 | Pro$^9$-α |
| 47 | 58.31 | d | 4.223 | dd | 2.144, 1.840 | 3.669, 3.553, 1.926, 2.144, (1.840) | Pro$^{10}$-α |
| 48 | 59.20 | d | 4.388 | dd | 2.012, 1.814 | 2.012 | Pro$^7$-α |
| 49 | 59.44 | d | 4.356 | dd | 2.031, 1.798 | 3.635, 1.880 | Pro$^4$-α |
| 50 | 73.50 | d | 3.227 | dd | 1.840, 1.416 | 0.903, 0.824 | Terpene-3 |
| | 73.51 | | | | | | |
| 51 | 97.93 | s | — | | — — | 3.154, 2.792, 0.972, 0.668 | Terpene-9 |
| | 97.91 | | | | | | |
| 52 | 100.90 | d | 6.598 | s | — | — | Terpene-3' |
| | 100.88 | | 6.596 | | | | |
| 53 | 112.62 | s | — | | — — | 6.593, 4.330 | Terpene-5' |
| | 112.55 | | | | | | |
| 54 | 116.92 | s | — | | — — | 3.154, 2.792, 6.597 | Terpene-1' |
| | 116.90 | | | | | | |
| 55 | 116.95 | d | 7.230 | s | 8.655 | (3.067), 2.937, 8.665 | His$^2$-ε |
| 56 | 117.26 | d | 7.322 | s | 8.771 | 3.092, 3.000, 8.771 | His$^5$-ε |
| 57 | 129.32 | s | — | | — — | 8.783, 7.322, 3.083 2.976, 4.585 | His$^5$-γ |
| 58 | 129.63 | s | — | | — — | 7.230, 3.064, 2.937, 4.592 | His$^5$-γ |
| 59 | 133.00 | s | — | | — — | 4.330 | 1–4' |
| | 132.98 | | | | | | |
| 60 | 133.63 | d | 8.655 | s | 7.230 | 7.230 | His$^2$-δ |
| 61 | 133.68 | d | 8.771 | s | 7.320 | 7.320 | His$^5$-δ |
| 62 | 153.60 | s | — | | — — | 6.597, 3.157, 2.792 | Terpene-2' |
| | 153.62 | | | | | | |
| 63 | 155.73 | s | — | | — — | (6.597), 3.154, 2.792, 4.330 | Terpene-6' |
| 64 | 168.11 | s | — | | — — | 6.597, 4.330, 4.881 | Terpene-7' |
| | 168.07 | | | | | | |
| 65 | 169.57 | s | — | | — — | 4.588, (4.223) | Pro$^9$-CO |
| 66 | 169.59 | s | — | | — — | 8.110, (4.570) | His$^5$-CO |
| 67 | 169.69 | s | — | | — — | 4.534, 1.444 | Leu$^8$-CO |
| 68 | 169.74 | s | — | | — — | 8.207, 2.937, 4.585 | His$^2$-CO |
| 69 | 169.97 | s | — | | — — | 8.513, 4.869, 2.190 8.499, 4.892, 2.182 | Met$^1$-CO |
| | 169.89 | | | | | | |
| 70 | 170.07 | s | — | | — — | 4.471, 1.733, 1.924, 4.356 | Gln$^3$-CO |
| 71 | 170.21 | s | — | | — — | 4.466, 1.722, 1.927, 4.388 | Gln$^6$-CO |
| 72 | 170.99 | s | — | | — — | 4.538, 4.388, 2.012, 1.844, 7.918 | Pro$^7$-CO |
| 73 | 171.32 | s | — | | — — | 8.138, 4.356, 2.003, 1.805, 4.570 | Pro$^4$-CO |
| 74 | 173.10 | s | — | | — — | 4.225, 2.144,1.840 | Pro$^{10}$-CO |
| 75 | 173.80 | s | — | | — — | 2.19, 1.93, 1.73 | 3-Gln-δ-CO |
| | 173.81 | | | | | | |
| 76 | 173.88 | s | — | | — — | 7.26, 2.19,1.93,1.73 | 4-Gln-δ-CO |
| | 173.86 | | | | | | |
| | OH | | 9.75 | br | | NOE: 6.598 | Terpene-2'-OH |
| | NH | | 8.506 | d | 4.585 | NOE: 4.869/4.692 | His$^2$-NH |
| | | | 8.496 | d | 4.590 | | |
| | NH | | 8.206 | d | 4.484 | NOE 3.072, 2.948, 4.588 | Gln$^3$-NH |
| | NH | | 8.135 | d | 4.563 | | His$^5$-NH |
| | NH | | 8.110 | d | 4.470 | NOE :4.570, (4.470), 1.727, (1.927) | Gln$^6$-NH |
| | NH | | 7.918 | d | 4.534 | NOE :4.388,1.827, 1.688, 1.427 | Leu$^8$-NH |
| | NH$_2$ | | 7.260 | s | (6.807) | | Gln$^6$-NH$_2$ |
| | | | 6.807 | s | (7.260) | | |
| | NH$_2$ | | 7.230 | s | (6.789) | | Gln$^3$-NH$_2$ |
| | | | 6.789 | s | (7.230) | | |

In one embodiment of the invention, the compounds of the formula (I) are obtainable by fermentation of *Memnoniella echinata* FH 2272, DSM 13195, or of one of its variants or mutants under suitable conditions in a culture medium until at least one memno peptide of the formula (I) is present in the culture medium, followed by subsequent isolation of the memno peptides.

The invention therefore furthermore relates to a process for the preparation of a compound of the formula 1, which comprises fermenting the microorganism *Memnoniella echinata* FH 2272, DSM 13195, or one of its variants or mutants under suitable conditions in a culture medium until at least one memno peptide of the formula (I) is present in the culture medium and then isolating the memno peptide from the culture medium.

In one embodiment, the strain FH 2272, DSM 13195, its mutants and/or variants are fermented in a nutrient solution (also called culture medium) comprising at least one source of carbon atoms and at least one source of nitrogen atoms and optionally comprising customary inorganic salts until memno peptides are present in the culture medium. The memno peptides may then be isolated from the culture medium and optionally separated into the individual active components and purified. In one embodiment, memno peptides accumulate in the culture medium, and are separated into individual components.

In another embodiment, at least one source of nitrogen atoms used for the culture medium is chosen from amino acids and peptides. The amino acids and peptides used as sources of nitrogen atoms may be the same as the group (A)n, as defined above.

The process according to the invention can be employed for fermentation on a laboratory scale (milliliter to liter range) and on industrial scale (cubic meter scale).

A strongly producing colony of Memnoniella echinata FH 2272 was grown. An isolate was deposited in the Deutsche Sammlung von Mikroorganismen und Zellkulturen GmbH, Mascheroder Weg 1B, D-38124 Braunschweig, Germany, according to the rules of the Budapest Convention on Dec. 9, 1999 under the following number: Memnoniella echinata FH 2272, DSM 13195.

Memnoniella echinata FH 2272, DSM 13195, has a brown-green mycelium and is characterized by the conidiophores characteristic of the genus Memnoniella.

Variants and mutants of the strain Memnoniella echinata FH 2272, DSM 13195, may also be employed to synthesize at least one compound of the memno peptides according to the invention. Such mutants can be produced in a manner known per se by physical means, for example irradiation, such as with ultraviolet rays or X-rays, or chemical mutagens, such as ethyl methanesulfonate (EMS), 2-hydroxy-4-methoxybenzophenone (MOB) or N-methyl-N'-nitro-N-nitrosoguanidine (MNNG). Possible variants include the closely related fungal species Stachybotrys, such as Stachybotrys atra, Stachybotrys chartarum or Stachybotrys complementi.

Screening for mutants and variants which synthesize at least one compound of the memno peptides according to the invention may be carried out according to the following scheme:
Separation of the mycelium after fermentation;
Extraction of the mycelium with an organic solvent;
Extraction of the memno peptides from the culture filtrate using solid phases
Analysis by means of HPLC, DC or by testing the biological activity.

The fermentation conditions described below apply to the fungus Memnoniella echinata FH 2272, the deposited isolate DSM 13195 and mutants and variants thereof.

In one embodiment, in a nutrient solution comprising at least one source of carbon atoms, casein peptone as a source of nitrogen atoms, and customary inorganic salts, Memnoniella echinata FH 2272, produces memno peptide A. In one embodiment, Memnoniella echinata FH 2272 is DSM 13195.

Possible sources of carbon atoms for aerobic fermentation include assimilable carbohydrates and sugar alcohols, such as glucose, lactose, sucrose, starches, dextrins, fructose, molasses, glycerol, galactose, and D-mannitol, and carbohydrate-containing natural products, such as malt extract. Possible sources of nitrogen atoms include, for example, amino acids; peptides; proteins; degradation products of amino acids, peptides and of proteins, such as casein, peptones, and tryptones; meat extracts; yeast extracts; peanut extracts; ground seeds, for example, of corn, wheat, beans, soy, and cotton; seed-containing compositions; distillation residues from alcohol production; meat meals; yeast extracts; ammonium salts, and nitrates. In one embodiment, at least one source of nitrogen atoms is chosen from synthetically obtained peptides and biosynthetically obtained peptides. The nutrient solution optionally comprises at least one inorganic salt. In one embodiment, the inorganic salt is chosen from chlorides, carbonates, sulfates and phosphates. The sulfates and phospates may be chosen from sulfates of the alkali metals, phosphates of the alkali metals, sulfates of the alkaline earth metals, and phosphates of the alkaline earth metals, wherein the alkaline earth metals are chosen from iron, zinc, cobalt and manganese.

The formation of the memno peptides according to the invention may proceed in a nutrient solution comprising casein peptone. In one embodiment, the nutrient solution comprises a concentration of casein peptone ranging from approximately 0.05 to 5%. Another embodiment comprises a concentration of casein peptone ranging from 0.1 to 1%. Still another embodiment comprises a concentration of casein peptone ranging from 0.2 to 5%. The nutrient solution may comprise glucose. One embodiment comprises a concentration of glucose ranging from 0.5 to 3%. The nutrient solution may also comprise cornsteep. In one embodiment the nutrient solution comprises a concentration of corn steep ranging from 0.05 to 1%. Another embodiment comprises a concentration of cornsteep ranging from 0.1 to 0.5%. The nutrient solution may comprise a trace of at least one component chosen from potassium chloride, magnesium sulfate and iron sulfate.

In one embodiment, the nutrient solution comprises casein peptone, glucose, cornsteep, and traces of potassium chloride, magnesium sulfate and iron sulfate. In another embodiment, the nutrient solution comprises a concentration of casein peptone ranging from approximately 0.05 to 5%, a concentration of glucose ranging from 0.5 to 3%, a concentration of corn steep ranging from 0.05 to 1%, and traces of potassium chloride, magnesium sulfate and iron sulfate. The data in percent are in each case related to the weight of the entire nutrient solution.

In this nutrient solution, Memnoniella echinata, which can be Memnoniella echinata FH 2272, DSM 13195, forms a mixture of memno peptides. Depending on the composition of the nutrient solution, the quantitative proportion of one or more of the memno peptides according to the invention may vary. Moreover, the synthesis of individual memno peptides can be controlled by the composition of the media such that a memno peptide may not be produced at all or may be produced in an amount below the detection limit of the microorganism.

The culturing of the microorganism may be carried out aerobically, i.e., for example, submerging with shaking or stirring in shaker flasks or fermenters, optionally with introduction of air or oxygen. It can be carried out in a temperature range from approximately 18 to 37° C., a narrower range from approximately 20 to 32° C., and a still narrower range of 25 to 30° C. The pH range should be between 6 and 8, such as between 6.5 and 7.5. In general, the microorganism is cultured under these conditions for a period of 24 to 300 hours, more generally 36 to 140 hours.

Advantageously, culturing may be carried out in a number of steps, i.e. at least one preculture may be prepared in a liquid nutrient medium, and may be then inoculated into the actual production medium, the main culture, for example, in the volume ratio 1:10. The preculture may be obtained, for example, by inoculating a mycelium into a nutrient solution and allowing it to grow for approximately 36 to 120 hours, such as for 48 to 72 hours. The mycelium can be obtained, for example, by allowing the strain to grow for approximately 3 to 40 days, such as 4 to 10 days, on a solid or liquid nutrient medium, for example, malt-yeast agar or potato dextrose agar (standard medium for mold fungi, for example, from Difco).

The course of the fermentation can be monitored by means of the pH of the cultures or of the mycelium volume as well as by chromatographic methods, such as thin-layer chromatography or high-pressure liquid chromatography or testing the biological activity. A compound according to the invention may be in both the mycelium and the culture filtrate, but the largest part is usually found in the culture filtrate.

The isolation process described below serves for the purification of the memno peptides according to the invention, for example, of memno peptide A. The isolation or purification of a memno peptide according to the invention from the culture medium may be carried out according to known methods taking into account the chemical, physical and biological properties of the natural substances. For the testing of the memno peptide concentrations in the culture medium or in the individual isolation steps, thin-layer chromatography, for example on silica gel, using isopropanol/25% strength $NH_3$ as an eluent or HPLC can be used. Detection in thin-layer chromatographic separation can be carried out, for example, by means of color reagents such as chlorosulfonic acid/glacial acetic acid, the amount of the substance formed expediently being compared with a calibration solution.

For the isolation of a memno peptide according to the invention, the mycelium is generally first removed from the culture broth using the usual procedures and the memno peptides are then extracted from the cell mass using an optionally water-miscible organic solvent. The organic solvent phase contains the natural substances according to the invention; it may be optionally concentrated in vacuo and the residue may be further purified as described below. In one embodiment, a memno peptide is extracted from the culture by adding solvent to the mixture of fungus and broth.

The culture filtrate may be optionally combined with the concentrate of the mycelium extract and extracted with a suitable, water-immiscible organic solvent, for example with n-butanol. The organic phase subsequently removed may be optionally concentrated in vacuo. To defat the valuable products, the concentrate can be diluted with a nonpolar solvent in which the compounds according to the invention are not very soluble, for example, with hexane, petroleum ether or diethyl ether. In this process, the memno peptides precipitate, and the lipophilic impurities remain dissolved and may be removed by customary solid/liquid phase separations.

The precipitate comprising the memno peptides may be dissolved in $\frac{1}{30}$ of the original volume of water/methanol. The precipitate dissolves completely in the course of this and may be lyophilized. The lyophilizate, subsequently called crude product, may comprise 5 to 50% memno peptides and may be employed for further isolation.

The further purification of at least one memno peptide according to the invention may be carried out by chromatography on suitable materials, for example, on molecular sieves, on silica gel, alumina, on ion exchangers or on adsorber resins or on reversed phases (RP). The memno peptides may be separated with the aid of this chromatography. The chromatography of the memno peptides may be carried out using buffered aqueous solutions or mixtures of aqueous and organic solutions.

Mixtures of aqueous and organic solutions are understood as meaning all water-miscible organic solvents, such as methanol, propanol and acetonitrile, in a concentration of 5 to 80% of solvent, more generally 20 to 50% of solvent or alternatively all buffered aqueous solutions which are miscible with organic solvents. The buffers to be used may be the same as indicated above.

Separation of the memno peptides on the basis of their differing polarity may be carried out with the aid of reversed phase chromatography, for example on MCI® (adsorber resin from Mitsubishi, Japan) or Amberlite XAD® (Toso Haas), or further hydrophobic materials, such as on RP-8 or RP-18 phases. Moreover, the separation can be carried out with the aid of normal-phase chromatography, for example on silica gel, alumina and the like.

Chromatography of the memno peptides may be carried out using buffered or acidified aqueous solutions or mixtures of aqueous solutions with alcohols or other, water-miscible organic solvents. In one embodiment, the organic solvent is chosen from propanol and acetonitrile.

Buffered or acidified aqueous solutions are understood as meaning at least one solution alone or in combination. For example, said at least one solution may be chosen from water, phosphate buffers, ammonium acetate, citrate buffers, and acids. In one embodiment, citrate buffer is in a concentration ranging from 0 to 0.5 M. Acids are chosen from formic acid, acetic acid, trifluoroacetic acid, and all commercially available acids known to the person skilled in the art. In one embodiment, the commercially available acid is in a concentration ranging from 0 to 1%. In yet another embodiment the concentration of acid is 0.1%.

Chromatography may be carried out using a gradient which begins with 100% of water and ends with 100% of solvent. At least one solvent is used. A mixture of two or more solvents may also be used. In one embodiment, a linear gradient is run from 20 to 50% of a solvent chosen from propanol and acetonitrile.

Alternatively, gel chromatography or chromatography on hydrophobic phases can also be carried out.

Gel chromatography may be carried out on polyacrylamide or copolymer gels, such as Biogel-P 2® (Biorad) or Fractogel TSK HW 40® (Merck, Germany or Toso Haas, USA).

A further, very effective process for the purification of the compounds according to the invention may be the use of ion exchangers. For example, the basic memno peptide A can be isolated very advantageously on cation exchangers, such as Fractogel® EMD $SO_3$. Buffer solutions between pH 5 and 8, such as between pH 6 and 7.5, can be used. Elution can be achieved, for example, using a rising salt gradient. In addition to water, it can also be advantageous to use mixtures of aqueous buffer solutions with an organic solvent as solvents. The proportion of the organic solvent may be between 10% and 90%, such as between 30 and 60%.

The sequence of the abovementioned chromatographic processes may be reversible.

A further, very effective purification step for memno peptides is crystallization. Memno peptides may be crystallized out from solutions in organic solvents and from mixtures of water with organic solvents. Crystallization may be carried out in a manner known per se, for example by concentrating or cooling saturated memno peptide solutions.

The memno peptides according to the invention are stable in the solid state and in solutions in the pH range between 3 and 8, for example 5 and 7, and can thus be incorporated into customary pharmaceutical preparations.

The formation of the nitrogen-containing memno peptides can be favored by adding the desired amino acids or peptides as precursor to the *Memnoniella echinata* cultures. It may be the peculiarity of the *Memnoniella echinata* species that they bind the amino groups of the amino acids and peptides supplied with synthesis of a five-membered ring lactam, usually of an isoindole ring system. This binding takes place either starting from the aldehyde precursor in the course of an oxidation or from the lactone oxidation stage in ring-opened form or the cyclic lactone form. This ability of the Memnoniella echinata to bind amines is completely surprising and can be used for obtaining protected, converted amine derivatives, such as of terpene derivatives of amino acids and peptides.

At least one compound of the memno peptides according to the invention may be suitable on account of their valuable pharmacological properties for use in human or veterinary medicine as pharmaceuticals.

The present invention thus relates to the use of the compound of the formula (I) or a physiologically tolerable salt thereof for the production of a cardiac remedy for the treatment or prophylaxis of cardiac insufficiency.

The compounds according to the present invention may also be used for the production of a pharmaceutical for the treatment of diseases wherein cardiac insufficiency is a primary or secondary cause of the disease such as, e.g., circulatory insufficiency.

The mechanism of action of the memno peptides is uncertain, but a significant effect was detected.

For the detection of the activators of SERCA2 which imitate the phosphorylation effect of PLB, a calorimetric test may be run which determines the activity of the $Ca^{2+}$ ATPase in dog heart microsomes in the presence of test substances. The test may be carried out in 96-well microtiter plates. The enzymatic release of inorganic phosphate from ATP, which forms a blue colored complex with ammonium molybdate which can be measured at 620 nm in a spectrophotometer, may be measured.

Memno peptide A activates SERCA2 in concentrations from 12.5 $\mu$M.

The memno peptides moreover have an antimicrobial action.

The present invention thus relates to the use of the compound of the formula (I) or a physiologically tolerable salt thereof for the production of a pharmaceutical for the treatment of microbial, for example bacterial, infections.

Table 3 shows some minimum inhibitory concentrations (MIC) of the antimicrobial spectrum of memno peptide A against some selected bacteria.

TABLE 3

| Strain | Resistance against: | MIC [$\mu$g/ml] |
|---|---|---|
| *Staphylococcus aureus* SG 511 | — | 16 |
| *Staphylococcus aureus* 285 | Penicillin | 16 |
| *Staphylococcus aureus* 503 | Penicillin | 16 |
| *Staphylococcus aureus* FH 1982 | Methicillin | 16 |
| *Staphylococcus aureus* 701E | Methicillin | 16 |
| *Staphylococcus aureus* 707E | Methicillin | 16 |
| *Staphylococcus aureus* 9 Tüb | Ofloxacin | 16 |
| *Staph. epidermidis* ZH 2c | — | 16 |
| *Staph. epidermidis* 763 | Methicillin | >16 |
| *Staph. epidermidis* 5747IIW | Methicillin | 32 |
| *Staph. epidermidis* 291 | Ofloxacin | 8 |
| *Staph. epidermidis* 799 | Ofloxacin | 8 |

TABLE 3-continued

| Strain | Resistance against: | MIC [$\mu$g/ml] |
|---|---|---|
| *Enterococcus faecium* Md8B | — | 8 |
| *Enterococcus faecium* VR1 | Vancomycin | >64 |
| *Enterococcus faecium* VR2 | Vancomycin | >64 |
| *Streptococcus pyogenes* VR3 | Vancomycin | >64 |
| *Streptococcus pyogenes* 308A | — | 8 |
| *Streptococcus pyogenes* 77A | — | 4 |

In addition to the antibacterial action, the compounds according to the invention exhibit weak antimycotic, i.e. antifungal, properties, for example against *Candida albicans.*

Moreover, the substances according to the invention have a certain favorable inhibitory action on glucose-6-phosphate translocase (G-6-P—TL), an enzyme which is of importance for glucose metabolism and thus for the treatment of diabetes mellitus. For example, the compound memno peptide A exhibits selective activities against G-6-P—TL, but it does not inhibit the coenzyme G-6-P phosphatase.

The present invention thus relates to the use of the compound of the formula (I) or a physiologically tolerable salt thereof for the production of a pharmaceutical for the therapy of diabetes mellitus.

The invention also relates to pharmaceutical preparations of at least one compound of the memno peptides according to the invention.

At least one compound of the memno peptides according to the invention, can generally be administered as such in undiluted form. Use as a mixture with suitable excipients or vehicles is one embodiment of the invention. Vehicles which can be used in pharmaceuticals may be the customary and pharmacologically tolerable vehicles and/or excipients.

In general, the pharmaceuticals according to the invention may be administered orally or parenterally, but rectal administration is also possible. Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form and preparations having protected release of active compound, in whose preparation vehicles and additives and/or excipients such as disintegrants, binders, coating agents, swelling agents, glidants or lubricants, flavorings, sweeteners or solubilizers are customarily used. Frequently used vehicles or excipients which may be mentioned are, for example, magnesium carbonate, titanium dioxide, lactose, mannitol and other sugars, talc, lactoprotein, gelatin, starch, vitamins, cellulose and its derivatives, animal or vegetable oils, polyethylene glycols and solvents, such as sterile water, alcohols, glycerol and polyhydric alcohols.

If appropriate, the dose units can be microencapsulated for oral administration in order to delay release or to extend it over a longer period of time, for example by coating or embedding the active compound in particle form in suitable polymers, waxes or the like.

In one embodiment, the pharmaceutical preparations may be produced and administered in dose units, each unit comprising, as active constituent, a specific dose of at least one compound of the memno peptides according to the invention. In the case of solid dose units such as tablets, capsules and suppositories, this dose can be up to approximately 500 mg, but more generally can be approximately 0.1 to 200 mg, and in the case of injection solutions in ampoule form up to approximately 200 mg, but usually approximately 0.5 to 100 mg, per day.

The daily dose to be administered is generally dependent on the body weight, age, sex and condition of the mammal. Under certain circumstances, however, higher or lower daily doses may also be appropriate. Administration of the daily dose can be carried out both by single administration in the form of an individual dose unit or else in a number of smaller dose units and by multiple administration of subdivided doses at specific intervals.

The pharmaceuticals according to the invention may be produced by bringing at least one compound of the memno peptides according to the invention into a suitable administration form using customary vehicles and, if appropriate, additives and/or excipients.

The invention is illustrated further in the following examples. Percentages relate to weight. Mixing ratios in the case of liquids refer to the volume, if no other details have been given.

The following examples are intended to illustrate the invention without limiting the scope thereof.

EXAMPLES

Example 1

Preparation of a Glycerol Culture of *Memnoniella echinata* FH 2272, DSM 13195.

100 ml of nutrient solution (malt extract 2.0%, yeast extract 0.2%, glucose 1.0%, $(NH_4)_2 HPO_4$ 0.05%, pH 6.0) in a sterile 300 ml Erlenmeyer flaskwere inoculated with the strain *Memnoniella echinata* FH 2272, DSM 13195, and incubated on a rotating shaker at 25° C. and 140 rpm for 7 days. 1.5 ml of this culture were then diluted with 2.5 ml of 80% strength glycerol and stored at −20° C.

Example 2

Preparation in an Erlenmeyer Flask of a Culture or a Preculture of *Memnoniella echinata* FH 2272, DSM 13195.

A sterile 300 ml Erlenmeyer flask containing 100 ml of the following nutrient solution, 10 g/l of glucose, 5 g/l of casein peptone, 1.7 g/l of liquid cornsteep, and 7 ml of trace element solution (10 g/l of KCl, 10 g/l of $MgSO_4 \times 7 H_2O$, 3.6 g/l of $FeSO_4 \times 7 H_2O$ and 6 g/l of $MgSO_4 \times H_2O$) was inoculated with a culture grown in a slant tube (same nutrient solution, but with 2% agar) or with 1 ml of a glycerol culture (see Example 1) and incubated at 180 rpm and 30° C. on a shaker. The maximum production of at least one compounds of the memno peptides according to the invention was achieved after about 120 hours. For the inoculation of 10 and 200 l fermenters, a submerged culture 48 to 96 hours old (inoculation quantity about 10%) from the same nutrient solution sufficed.

Example 3

Preparation of the Memno Peptides.

A 30 l fermenter was operated under the following conditions:

| | |
|---|---|
| Nutrient medium: | 10 g/l of glucose |
| | 0.5 g/l of casein peptone |
| | 1.7 g/l of liquid cornsteep |
| | 7 ml of trace element solution |
| | pH 6.5 (before sterilization) |
| Trace element solution: | KCl 10 g/l, $MgSO_4 \times 7 H_2O$ 10 g/l, |
| | $FeSO_4 \times 7 H_2O$ 3.6 g/l and $MnSO_4 \times H_2O$ 6 g/l |
| Incubation time: | 45 hours |
| Incubation temperature: | 28° C. |

-continued

| | |
|---|---|
| Stirrer speed: | 300 rpm |
| Aeration: | 15 l min$^{-1}$ |

Foam formation was optionally suppressed by repeated addition of ethanolic polyol solution. The production maximum was achieved after about 35 to 70 hours.

Example 4

Isolation of the Memno Peptide Mixture from the Culture Solution of *Memnoniella echinata* FH 2272, DSM 13195.

After completion of the fermentation of *Memnoniella echinata* FH 2272, DSM 13195, the culture broth of the fermenter, obtained according to Example 3 (200 liters) was filtered with addition of about 2% filter aid (e.g. Celite®) and the cell mass (22 liters) was extracted with 66 liters of methanol. The methanolic solution containing the valuable substance was freed of the mycelium by filtration and concentrated in vacuo. The concentrate was diluted with water and applied to a prepared, 17 liter MCI GEL, CHP20P column together with the culture filtrate (180 liters). It was eluted with a gradient of water after 60% propan-2-ol in water. The column flow (25 liters per hour) was collected in fractions (10 liters each) and the memno peptide-containing fractions (from 25% to 30% propan-2-ol) were combined.

Concentration in vacuo afforded 20 liters of a brown solution. Six liters of cation exchanger, Fractogel® EMD $SO_3$, equilibrated at pH 7 with potassium phosphate buffer were packed into a column (125 mm×500 mm). After loading the ion exchanger with 20 liters of the concentrate described above, it was eluted with a gradient of 10 mM potassium phosphate buffer, pH 7, after 1 M NaCl in 10 mM potassium phosphate buffer, pH 7 in water/methanol (1:1). The column flow, i.e. the unbound material, contained the neutral memno peptides (49 g). The column flow was 12 liters per hour; 1 liter portions were collected in fractions during the gradient elution. With 0.75 M NaCl (fractions 31 and 32), memno peptide A was obtained. Fractions 31 and 32 were combined and concentrated to approximately 500 ml in vacuo.

Example 5

Enrichment of Memno Peptide A by Gel Chromatography.

8 g of the product obtained according to Example 4 were applied to a column of 3.9 liters capacity packed with Fractogel® TSK HW-40 s (width×height=10 cm×50 cm). The eluent:methanol/water (1:1) was pumped through the column at a flow rate of 20 ml per minute and the column outflow was collected in fractions (20 ml). The memno peptides A were found mainly in fractions 75 to 85. They were combined and freed of the methanol in vacuo. They afforded 0.9 g of active compound mixture.

Example 6

HPLC System for the Detection of the Memno Peptides.

The system described below allowed purity testing and also separation and quantification of the memnoterpenes, for example in the crude mixture or in the culture filtrates.
Eluent: 0.1% trifluoroacetic acid in 32% acetonitrile.
Column: Nucleosil 100$C_{18}$AB 250/4, Macherey-Nagel.
Flow: 1.0 ml/min
Detection: Ultraviolet light absorption at 210 nm.

Under the conditions indicated, memno peptide A can thus have the following retention time:
Memno peptide A: 7.0 minutes.

Example 7
Purification of Memno Peptide A.

500 ml of solution of memno peptide A isolated and enriched according to Example 5 were applied to a 500 ml Nucleosil®100-7 $C_{18}$AB column and chromatographed using a gradient of 25 to 50% acetonitrile in 0.05% trifluoroacetic acid/water. The flow of the eluent was 50 ml per minute; the fraction size 50 ml. Memno peptide A was found in fractions 71 to 88. Repeated purification of the combined fractions with a constant solvent concentration of 28% of acetonitrile in 0.05% trifluoroacetic acid afforded >95% of pure memno peptide C after freeze drying (100 mg).

Characterization of Memno Peptide A:

10 μg of memno peptide A were hydrolyzed in constant-boiling hydrochloric acid and investigated in an amino acid analyzer. The following customary amino acids were found:

| | |
|---|---|
| Glutamic acid | 11 nMol |
| Proline | 22 nMol |
| Histidine | 10 nMol |
| Leucine | 5.6 nMol |
| Methionine oxide | 5.5 nMol |

Ultraviolet absorption: $\lambda_{max}$ at 269 nm, 305 nm (shoulder).

The high-resolution FAB mass spectrum showed an intensive MH$^+$ at m/z 1565.7819 Da, in good agreement with the calculated mass (for $C_{76}H_{109}N_{16}O_{18}S$, monoisotopic) of 1565.7827 Da. The MS/MS fragmentation corresponded to the formula (IVa).

$R_3$ and $R_4$ together are double bonded O, or are each H, or H and OH, or H an O—$C_1$–$C_4$-alkyl:

$R_5$ and $R_7$ are each H:

$R_8$ is chosen from H, OH, $C_1$–$C_4$-alkyl, and O—$C_1$–$C_4$-alkyl:

$R_{10}$ is H or glycosidically bonded sugar;

A is a natural amino acid selected from Gly, Ala, Val, Leu, Ile, Pro, Ser, Thr, Phe, Tyr, Trp, Lys, Arg, Asp, His, Glu, Asn, Gln, Cys, and Met:

n is an integer chosen from 1 to 12, wherein each A in A(n) is the same or different from every other A:

wherein the nitrogen atom in the isoindole ring of formula V is the N-terminal amine nitrogen of the first acid of the A(n) group;

or a salt thereof.

2. A compound according to claim 1, or a salt thereof, wherein (A)n is a peptide chain having 2 to 12 natural amino acids as defined in claim 1.

3. A compound according to claim 1, or a salt thereof, wherein (A)n is a peptide chain having the amino acid sequence: Met-His-Gln-Pro-His-Gln-Pro-Leu-Pro-Pro (SEQ ID NO: 1) wherein the Met is optionally oxidized to form a sulfoxide.

What is claimed is:

1. A compound of formula V

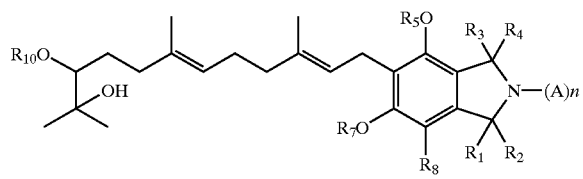

wherein $R_1$ and $R_2$ together are double bonded O, or are each H, or H and OH, or H and O—$C_1$–$C_4$-alkyl:

4. A compound according to claim 1, or a salt thereof, wherein $R_{10}$ is an aldohexose.

5. A compound according to claim 1, or a salt thereof, obtainable by cultivation of *Memnoniella echinata* FH 22727, or DSM 13195, under suitable conditions in a culture medium until a compound according to claim 1 is present in the culture medium, and said compound is subsequently isolated.

6. A compound according to claim 5, further comprising conversion of said compound into at least one physiologically tolerable salt.

7. A compound, memno peptide A, $C_{76}H_{108}N_{16}O_{18}S$, of the formula IVa:

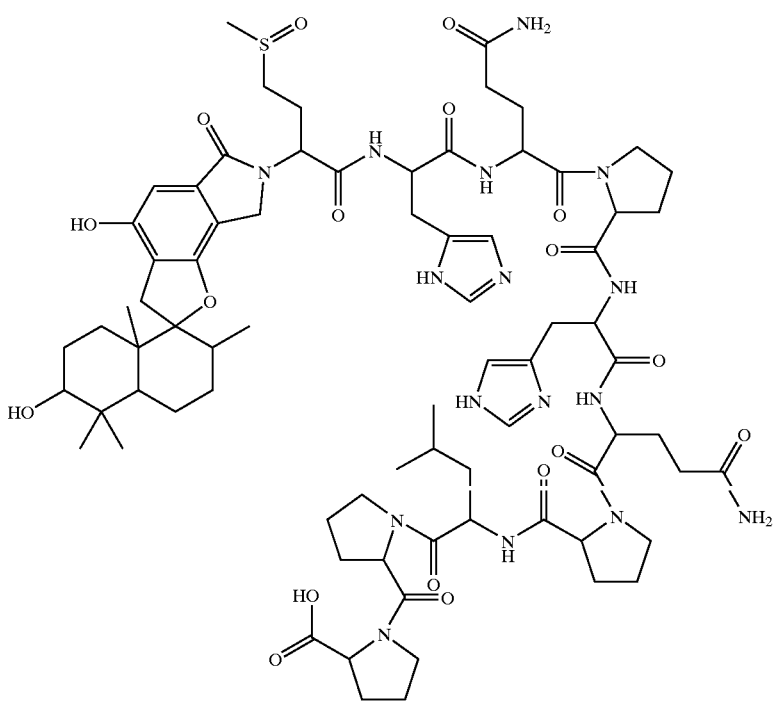

IVa or a salt thereof.

8. A compound according to claim 1, wherein the group-(A)n comprises a part of the amino acid sequence for casein.

9. A compound according to claim 8, wherein (A)n is the amino acid sequence: Met His Gln Pro His Gln Pro Leu Pro Pro (SEQ ID NO:1).

10. A composition comprising at least one compound of formula V, wherein said compound is defined according to claim 1, and optionally a vehicle, excipient, or combinations thereof.

11. A composition according to claim 10, wherein said composition is a pharmaceutical composition and said vehicle, excipient, or combinations thereof are pharmaceutically acceptable.

12. A composition comprising at least one compound of formula IVa, as defined in claim 7, and optionally a vehicle, excipient, or combinations thereof.

13. A composition according to claim 12, wherein said composition is a pharmaceutical composition and said vehicle, excipient, or combinations thereof are pharmaceutically acceptable.

14. A process for making a compound of formula V, or a salt thereof, as defined in claim 1, comprising cultivation of *Memnoniella echinata* FH 2272, or DSM 13195, under suitable conditions in a nutrient solution comprising at least one source of carbon atoms and at least one source of nitrogen atoms until at least one compound of formula V is present in the nutrient solution and said compound is subsequently isolated.

15. A process according to claim 14, further comprising, conversion of the compound into at least one physiologically tolerable salt.

16. A process according to claim 14, wherein said cultivation occurs under aerobic conditions.

17. A process according to claim 14, wherein said at least one source of nitrogen atoms is chosen from amino acids and peptides.

18. A process according to claim 14, wherein said nutrient solution comprises casein peptone at a concentration ranging from about 0.05% to 5% by weight of the nutrient solution.

19. A process according to claim 14, wherein said nutrient solution comprises glucose at a concentration ranging from 0.5% to 3% by weight of the nutrient solution.

20. A process according to claim 14, wherein said nutrient solution comprises corn steep at a concentration ranging from 0.05 to 1% by weight of the nutrient solution.

21. A process according to claim 14, wherein said nutrient solution comprises casein peptone, glucose, cornsteep, and traces of potassium chloride, magnesium sulfate and iron sulfate.

22. A process according to claim 14, wherein said cultivation is carried out at a temperature ranging from about 18 to 37° C.

23. A process according to claim 14, wherein said cultivation is carried out at a pH ranging from 3.0 to 8.0.

24. A process according of claim 14, wherein said cultivation is carried out during a time period ranging from 24 to 300 hours.

25. A process according to claim 14, wherein said cultivation is carried out in submerged conditions.

26. A process according to claim 14, wherein said compound is isolated from at least one component chosen from culture filtrates and mycelia.

27. A process for treating cardiac insufficiency in a mammal, comprising administering to the mammal in need thereof an effective amount of at least one compound of formula V, or a salt thereof, as defined in claim 1.

28. A process for treating cardiac insufficiency in a mammal, comprising administering to the mammal in need thereof an effective amount of at least one compound of formula IVa, or a salt thereof, as defined in claim 7.

29. A process for treating a disease in a mammal wherein cardiac insufficiency is a primary or secondary cause, comprising administering to the mammal in need thereof an effective amount of at least one compound of formula V, or a salt thereof, as defined in claim 1.

30. A process for treating a disease in a mammal wherein cardiac insufficiency is a primary or secondary cause, comprising administering to the mammal in need thereof an effective amount of at least one compound of formula IVa, or a salt thereof, as defined in claim 7.

31. A process for treating diabetes mellitus in a mammal, comprising administering to the mammal in need thereof an effective amount of at least one compound of formula V, or a salt thereof, as defined in claim 1.

32. A process for treating diabetes mellitus in a mammal, comprising administering to the mammal in need thereof an effective amount of at least one compound of formula IVa, or a salt thereof, as defined in claim 7.

33. A process for treating a microbial infection in a mammal, comprising administering to the mammal in need thereof an effective amount of at least one compound of formula V, or a salt thereof, as defined in claim 1.

34. A process for treating a microbial infection in a mammal, comprising administering to the mammal in need thereof an effective amount of at least one compound of formula IVa, or a salt thereof, as defined in claim 7.

* * * * *

UNITED STATES PATENT AND TRADEMARK OFFICE
CERTIFICATE OF CORRECTION

PATENT NO.  : 6,627,604 B2
DATED       : September 30, 2003
INVENTOR(S) : Vertesy et al.

It is certified that error appears in the above-identified patent and that said Letters Patent is hereby corrected as shown below:

Column 19,
Line 67, "O-$C_1$-$C_4$-alkyl:" should read -- O-$C_1$-$C_4$-alkyl; --.

Column 20,
Line 2, "H an" should read -- H and --; and "O-$C_1$-$C_4$-alkyl:" should read -- O-$C_1$-$C_4$-alkyl; --.
Line 3, "each H:" should read -- each H; --.
Lines 5-6, "O-$C_1$-$C_4$-alkyl:" should read -- O-$C_1$-$C_4$-alkyl; --.
Line 11, "Met:" should read -- Met; --.
Line 14, "other A:" should read -- other A; --.
Line 16, "first acid" should read -- first amino acid --.
Line 24, after "thereof", insert a comma.
Line 25, ",wherein" should read -- wherein --.
Line 58, "22727" should read -- 2272 --.

Column 21,
Lines 32-33, "group-(A)n" should read -- group -(A)n --.
Line 54, after "FH 2272", delete the comma.

Column 22,
Line 49, "according of" should read -- according to --.

Signed and Sealed this

Ninth Day of March, 2004

JON W. DUDAS
*Acting Director of the United States Patent and Trademark Office*

SEQUENCE LISTING

<160> NUMBER OF SEQ ID NOS: 1

<210> SEQ ID NO 1
<211> LENGTH: 10
<212> TYPE: PRT
<213> ORGANISM: artificial sequence
<220> FEATURE:
<221> NAME/KEY: misc_feature
<223> OTHER INFORMATION: Description of Artificial Sequence:
      Memnoniella echinata, FH 2271, DSM 1319

<400> SEQUENCE: 1

Met His Gln Pro His Gln Pro Leu Pro Pro
1               5                   10